US005679393A

United States Patent [19]
Laur et al.

[11] Patent Number: 5,679,393
[45] Date of Patent: Oct. 21, 1997

[54] METHOD OF PREPARING FAT FRACTIONS OF VEGETABLE ORIGIN ENRICHED WITH UNSAPONIFIABLE MATERIALS AND USE OF SAID FRACTIONS FOR PREPARING COSMETIC AND/OR PHARMACEUTICAL COMPOSITIONS, IN PARTICULAR DERMATOLOGICAL COMPOSITIONS

[75] Inventors: Joël Laur, Merignac; Anne Castera, Pessac; François Mordret, Gradignan; Xavier Pages-Xatart-Pares, Cestas; Jean-Michel Guichard, Carrieres sur Poissy, all of France

[73] Assignee: Deslog, Paris, France

[21] Appl. No.: 513,874

[22] PCT Filed: Mar. 18, 1994

[86] PCT No.: PCT/FR94/00301

§ 371 Date: Oct. 25, 1995

§ 102(e) Date: Oct. 25, 1995

[87] PCT Pub. No.: WO94/21764

PCT Pub. Date: Sep. 29, 1994

[30] Foreign Application Priority Data

Mar. 19, 1993 [FR] France .................................. 93 03226

[51] Int. Cl.$^6$ .............................. C11B 3/00; A61K 6/00; A61K 31/20
[52] U.S. Cl. ..................... 426/417; 424/401; 514/558
[58] Field of Search .................... 426/417; 424/401; 514/558

[56] References Cited

U.S. PATENT DOCUMENTS 3,012,891 12/1961 Best et al. ............................. 426/607

*Primary Examiner*—John W. Rollins
*Attorney, Agent, or Firm*—Dennison, Meserole, Pollack & Scheiner

[57] ABSTRACT

A process for preparation of a fat fraction of vegetable origin enriched with unsaponifiable materials. A fat of vegetable origin is treated with a hot polar solvent of the ketone type to obtain a first fraction insoluble in the hot ketone solvent which is rich in unsaponifiable materials, and a second fraction which is a solution of hot soluble materials. The first fraction is then separated from the second fraction, and the second fraction is subjected to a crystallization in a crystallization solvent at a temperature below 0° C., followed by filtering to obtain a filtrate. The crystallization solvent is then evaporated from the filtrate to obtain a further fraction rich and unsaponifiable materials.

26 Claims, No Drawings

METHOD OF PREPARING FAT FRACTIONS OF VEGETABLE ORIGIN ENRICHED WITH UNSAPONIFIABLE MATERIALS AND USE OF SAID FRACTIONS FOR PREPARING COSMETIC AND/OR PHARMACEUTICAL COMPOSITIONS, IN PARTICULAR DERMATOLOGICAL COMPOSITIONS

The present invention relates to a novel process for the preparation of fat fractions of vegetable origin enriched with unsaponifiable materials. It further relates to the use of these fractions and mixtures thereof for the preparation of cosmetic and/or pharmaceutical compositions, especially dermatological compositions.

According to the definition given in the standard NF T 60-205-1, which describes the method of determining content (reference method), unsaponifiable materials are all the substances present in the product which, after saponification of the latter with potassium hydroxide and extraction with a specified solvent, are not volatile under the specified operating conditions.

Thus, as stated in said standard, unsaponifiable materials include natural constituents of fats, such as sterols, aliphatic and terpene higher alcohols and hydrocarbons, and the foreign organic substances they may contain which are extracted by the solvent and are non-volatile at 103° C. (for example mineral oils).

In the present disclosure, "unsaponifiable materials" will denote unsaponifiable materials as defined above.

The pharmaceutical and cosmetic industries have been using fat extracts of vegetable origin since earliest times. A number of years ago it became apparent in these industries that particularly valuable biological properties resulted from the use of vegetable fats or extracts of vegetable fats rich in unsaponifiable materials.

Certain vegetable oils, such as avocado, soya, colza, olive and, in particular, shed oils, are known to be particularly rich in unsaponifiable materials and/or to contain, in these unsaponifiable materials, one or more constituents of interest in the aforesaid sectors.

Numerous processes are known for the fractionation of fats of vegetable origin for the purpose of recovering or removing some of their components in order to use them in different industries, in particular in the food industry and in the pharmaceutical and cosmetic industries.

Shea has proved of very particular interest.

Numerous processes for the fractionation of shea oil have been described. Most of these processes use aliphatic ketones and propose the removal of the karitene in order to recover the ketone-soluble fraction usable in the cocoa industry as a cocoa butter substitute and/or equivalent.

In contrast to the processes mentioned above, but still with the aim of recovering a product usable in the food industry, patent U.S. Pat. No. 4,103,039 proposes dissolving the shea fat in hot ethanol, removing the ethanol-insoluble fraction and leaving the remaining solution to cool to a temperature of between 20° and 60° C. so as to separate said solution into two distinct liquid layers, the upper layer being oil-poor and the lower layer oil-rich. In said document the oil-rich layer is subsequently dissolved in an organic solvent such as hexane and then subjected to a fractionation operation by crystallization from a solvent such as hexane.

Said document makes no attempt to achieve any enrichment of one of the fractions with unsaponifiable materials, its aim being to produce a cocoa butter substitute for use in food. Furthermore, the process described in said document has to use two solvents, namely ethanol, in which the gums are insolubilized, and then hexane, in which the fractionation takes place.

According to one of these essential characteristics, the present invention relates to a process for the preparation of fat fractions of vegetable origin enriched with unsaponifiable materials, characterized in that it consists in treating said fat of vegetable origin with a polar solvent of the ketone type in order to recover on the one hand a hot-insoluble fraction (I), which constitutes a first fraction rich in unsaponifiable materials, and a solution of a so-called hot-soluble fraction (S) in the ketone solvent, subjecting said hot-soluble fraction (S) to a crystallization step in a so-called crystallization solvent at a temperature below 0° C. and filtering the resulting product in order to recover a filtrate (F), which, after evaporation of the crystallization solvent, constitutes a second fraction (I') rich in unsaponifiable materials.

The fats which can be treated by the process according to the invention are any fats of vegetable origin.

These may be crude or refined fats originating from seeds (for example colza, soya) or fruits (for example shea, avocado, olive) of oleaginous plants.

The process according to the invention can also be applied to the treatment of vegetable butters such as mahua or Borneo butter and sal butter, mango stone fat, allanblackia, kokum or Goa tallow, dhupa fat, and butters or oils originating from the families of the sapotaceae and dipterocarpaceae, as well as from tropical plants.

The fats which will preferably be chosen are those which are naturally rich in unsaponifiable materials and/or those in which the unsaponifiable materials contain one or more constituents capable of having valuable properties in the field of cosmetology, pharmacy or medicine.

If the fat of vegetable origin subjected to the process of the invention is a crude fat, it can be obtained by conventional techniques, particularly pressure techniques in the case of olive, shea or avocado, or pressure/extraction techniques, for example in the case of soya, avocado or colza. It can also be obtained by manual techniques, as in the case of shea butter.

The fat of vegetable origin subjected to the process of the invention can also undergo a refining step beforehand.

Examples of refining processes which may be mentioned are the conventional processes of chemical or physical refining or the more specialized processes for the refining of shea butter, which make it possible in particular to retain the maximum amount of unsaponifiable materials.

The chemical refining which is advantageously used, being applied to the vegetable fats before they are subjected to the process according to the invention, may be any conventional chemical refining process, in particular any process comprising the following steps:

step 1: so-called demucilagination step involving insolubilization of the phosphatides with water, generally in the presence of acid, most frequently phosphoric acid, and separation by decantation or centrifugation (continuous process);

step 2: neutralization of the free fatty acids from the oil by addition of a sodium hydroxide solution and separation of the soaps formed (called neutralization pastes), most frequently by centrifugation followed by several washes with water, steps 1 and 2 often being performed simultaneously;

step 3: decolorization with activated bleaching clays at about 100° C. under reduced vacuum, and filtration;

step 4: deodorization operation necessary for removing the compounds responsible for the flavors of an oil and for producing an edible refined oil with good keeping qualities. This operation is carried out in an apparatus called a deodorizer, the procedure involving heating of the oil to a high temperature (180°–220° C.) under a vacuum of the order of 4 torr (i.e. about 532 Pa) and a massive injection of steam.

A vegetable fat which has undergone a physical refining process beforehand can also be subjected to the process according to the invention.

Physical refining is in fact understood as a variant of the chemical refining process explained above, the difference being that the neutralization step with sodium hydroxide is not performed and that the removal of the free fatty acids from the oil is effected during the deodorization step, which is then performed as a neutralization operation at a higher temperature in adapted equipment.

In the case of shea, it is advisable to carry out the process without demucilagination by means of a double chemical neutralization and a light treatment with clay under mild conditions so as to minimize the losses of unsaponifiable material and/or several of its constituents.

The treatment with a polar solvent of the ketone type is preferably carried out at the boiling point of said solvent.

Any ketone containing at most 10 carbon atoms can be chosen as the ketone solvent.

Acetone and methyl isobutyl ketone may be mentioned as examples of preferred ketone solvents according to the invention. Acetone will preferably be chosen.

The amount of ketone solvent will be determined as a function of the vegetable fat treated. What will be determined in particular is the optimum amount enabling a selective recovery of the insoluble materials, in particular the karitene, while at the same time avoiding the use of an excessive amount of solvents so as not to interfere with the subsequent crystallization step.

As an example in the case of the treatment of shea butter, an amount of about 1 l of acetone will be used per 200 g of shea butter.

To ensure a good extraction of all the products soluble in the ketone solvent, boiling will be maintained for a sufficient time, advantageously of the order of 30 min, before the insoluble part is separated off by decantation and then filtration or centrifugation.

The crystallization step at a temperature below 0° C. can be carried out in any solvent for the fraction soluble in the hot ketone solvent used in the first step of the process according to the invention.

Acetone, methyl isobutyl ketone, hexane, dichloromethane, dichloroethane, ethyl acetate or isopropanol may be mentioned in particular as examples of such solvents.

If the solvent used for the crystallization step is a different solvent from that used in the previous hot insolubilization step, the ketone solvent used for the hot insolubilization is removed prior to dissolution in the crystallization solvent. This removal can be effected in conventional manner by evaporation of the ketone solvent under vacuum.

In one particularly advantageous variant of the process according to the invention, the solvent used for the crystallization step is the same as that used for the hot dissolution step.

In one particularly advantageous variant, the crystallization step is carried out directly on the ketone solution recovered after removal of the fraction insoluble in this hot solvent.

In one particularly advantageous variant, acetone is used as the solvent in both the hot dissolution and crystallization steps.

In one advantageous embodiment, dilutions of plant material in the ketone solvent of between 5 and 30% by weight, advantageously of the order of 20% by weight, are used.

Acetone will be chosen as the preferred solvent for this step.

The crystallization temperature will preferably be situated well below 0° C., preferably between –15° and –30° C. However, lower temperatures may also be used.

If the crystallization step is carried out on the laboratory or pilot scale as a batch process, the crystallization time is of the order of 12 to 24 h. However, the use of an industrial crystallizer, making it possible to fix a cooling scale down to the desired crystallization temperature, followed by maturation at this temperature prior to filtration, enables the process to be optimized and, in particular, enables the duration of the operation to be shortened.

After crystallization, the product is filtered to recover on the one hand a filtrate (F) and on the other hand a solid fraction called a concrete, which contains part of the solvent.

After evaporation of the solvent, this concrete has very similar physicochemical characteristics to that of the starting vegetable fat, apart from the considerably reduced content of unsaponifiable materials. This offers a significant advantage, particularly in the case of shea butter for example, since it provides a product which is of greater value in the food sector than unconverted shea butter, especially for the manufacture of cocoa butter substitutes and/or equivalents, where the rheological and melting characteristics of the fat, which are closely related to the fatty acid and triglyceride composition, are determining factors.

The filtrate is then subjected to a solvent removal step, for example a vacuum evaporation step. This step leads to the recovery of a second fraction rich in unsaponifiable materials (I').

One advantage of the process according to the invention, as described above, is that it yields two fractions rich in unsaponifiable materials. These two fractions can then be totally or partially mixed to give novel mixtures enriched with unsaponifiable materials. Thus, in one particularly advantageous variant, the process according to the invention also comprises a step for mixing at least part, preferably all, of each of the two fractions enriched with unsaponifiable materials.

Thus the fraction (I'), or part of this fraction, is advantageously mixed with the first fraction rich in unsaponifiable materials, consisting of the part insoluble in hot acetone (fraction I), or with part of this fraction.

In one advantageous variant of the process according to the invention, the fraction (I) is dissolved in a solvent before being mixed with the fraction (I').

A solvent belonging to the family of the chlorinated solvents, such as chloroform, methylene chloride, dichloromethane or dichloroethane, or a chlorofluorinated solvent of the flugen type, will be chosen as the preferred solvent for dissolving the fraction (I).

After mixing of the fraction (I') and the fraction (I), or desired amounts of these fractions, and evaporation of the solvent, the final product recovered constitutes a fraction of the treated plant material which is particularly enriched with unsaponifiable materials.

It can be seen that one advantage of the process of the invention is that it provides, by mixing of the two fractions, fractions enriched with unsaponifiable materials whose content of unsaponifiable materials may be modified by varying the proportions of the two fractions as well as the recrystallization temperature.

Thus, by way of example, the treatment of 3 kg of a neutralized and decolorized shea butter containing 0.42% of oleic acid and 6.4% of unsaponifiable materials, under the conditions of Example 6 below, using the process according to the invention and after mixing of the fractions (I) and (I'), will give 150 g of a fraction enriched with unsaponifiable materials which contains 2.8% of oleic acid and at least 48% of unsaponifiable materials.

The mixtures of fractions enriched with unsaponifiable materials which are obtained by the process of the invention, very particularly those obtained from shea, prove to be of particular value as the active principle of cosmetic and/or pharmaceutical compositions, especially dermatological compositions.

Thus, according to a second feature, the invention relates to the use of the above-described mixtures of fractions enriched with unsaponifiable materials for the preparation of a cosmetic or pharmaceutical composition, especially dermatological composition, with anti-free radical and/or anti-elastase activity.

In one variant, the abovementioned composition affords good protection against the conventional aggressions to which the skin is subjected, namely chemical, thermal and mechanical aggressions and aggressions resulting from exposure to visible and ultraviolet light radiation.

In another variant, the abovementioned composition has antiinflammatory activity.

According to another of these features, the invention relates to a cosmetic composition containing, as the active ingredient, a cosmetically active amount of a mixture of fractions enriched with unsaponifiable materials which is obtained by treating a shea butter by the process of the invention.

According to another of these features, the invention relates to a pharmaceutical composition, especially dermatological composition, comprising, as the active ingredient, a pharmaceutically effective amount of a mixture of fractions enriched with unsaponifiable materials which is obtained by the process of the invention.

According to both the above features, it will be preferable to use fractions rich in unsaponifiable materials which are obtained by treating shea butter.

The mixtures of unsaponifiable fractions will preferably contain 18 to 50% by weight of unsaponifiable compounds, preferably 20 to 50% and particularly preferably of the order of 30%.

These mixtures will be incorporated at concentrations of between 0.5 and 99% by weight, preferably of between 2 and 60%, into a cosmetically or pharmaceutically acceptable excipient, vehicle or carrier.

As seen above, the value of the cosmetic or pharmaceutical compositions, especially dermatological compositions, using the mixtures of fractions enriched with unsaponifiable material which are obtained by the process described above, results mainly from two advantages:

1. the enriched fraction or fractions obtained have an identical appearance to that of a semiconcrete natural fat which is easy to use and has an attractive appearance;
2. because of their great richness in unsaponifiable material, said fractions afford good protection against the conventional aggressions to which the skin is subjected, namely chemical, thermal and mechanical aggressions and aggressions resulting from exposure to visible and ultraviolet light radiation.

Good anti-free radical properties, which are far superior to those of starting fats not enriched with unsaponifiable material by the process described above, have thus been demonstrated especially on emulsions produced with the abovementioned mixtures, and the mixtures themselves, by tests performed in vitro.

The anti-free radical activity was advantageously demonstrated using the so-called "erythrocyte" test, the principle of which is described below and which enables the anti-free radical power of a molecule to be evaluated in vitro. Its capacity to inhibit the hemolysis of erythrocytes subjected to a free-radical attack is monitored.

The water-soluble free-radical generator 2,2'-zobisdiamidinopropane hydrochloride is used for this test.

More precisely, this test consists in subjecting erythrocytes, isolated from their plasma, to an aggression of the oxidative type under controlled and standardized conditions which enable them to utilize all their enzymatic and molecular equipment to resist this aggression until the cell membrane is modified, this being followed by bursting and lysis of the cell.

The hemoglobin is then measured by spectrophotometry.

The resistance of the population of erythrocytes tested is then expressed as the time taken for 50% of the hemoglobin content to be released (T50).

A percentage protection against hemolysis is calculated. The calculation is performed by comparing the T50 (50% hemolysis) of the tests with that of the control.

The higher the T50 of a test, the greater is the protection; hemolysis has been delayed. Conversely, a low T50 indicates that the molecule is more pro-oxidizing.

Thus, with the mixtures enriched with unsaponifiable material which are obtained according to the invention, T50 values of 128 to 196 are attained.

Likewise, good antielastase properties, again superior to those of starting fats not enriched with unsaponifiable compounds by the process described above, have been demonstrated on the mixtures of the invention, in particular by means of the in vitro tests described below, which make it possible to demonstrate the inhibition of human leukocyte elastase (HLE).

The following two tests were mainly used:
a) Use of N-methoxysuccinyl-(ala)$_2$-pro-val-paranitro-anilide, a synthetic substrate specific for HLE In this test, the hydrolysis of the substrate by leukocyte elastase is monitored by spectrophotometry for five minutes.

Different concentrations of inhibitors are incubated in the reaction buffer in the presence of enzyme, and the substrate is then added.

The percentage inhibitions are calculated relative to a reference curve: hydrolysis of the substrate in the absence of inhibitor.

The inhibitor concentration at which 50% inhibition of the enzyme is obtained (=IC50) is also measured.
b) Use of fibrous elastin, a natural substrate for HLE This test corresponds to more physiological conditions.

In this test, different concentrations of inhibitors are incubated in the reaction buffer in the presence of the enzyme, and 150 µg of radiolabeled fibrous elastin are then added.

The samples are incubated at 37° C., with shaking. The hydrolysis of the substrate is measured after 1, 2, 4 and 6 hours of incubation.

The undigested (insoluble) elastin is separated from the hydrolyzed (soluble) elastin by centrifugation at 10,000 rpm for 30 seconds. The radioactivity originating from the hydrolysis of the elastin is measured in 50 µl of supernatant.

The percentage inhibitions and the IC50 values are measured in the same way as for analysis with the synthetic substrate.

The mixtures enriched with unsaponifiable material, according to the invention, result in percentage inhibitions of human leukocyte elastase of 16 to 80%.

The techniques referred to above make it possible to know whether the molecule or molecules are of value in the field of inflammation. In fact, in an inflammatory pathological condition, there is a local production of various free radicals and an increase in the synthesis of human leukocyte elastase. These tests are performed in vitro but are adaptable in vivo or ex vivo; they are recognized as methods of cosmetic objectification.

In one advantageous variant of the invention, the cosmetic and/or pharmaceutical compositions, especially dermatological compositions, can also contain other components which are known for their protective action against skin aggressions and which act synergistically with the mixtures rich in unsaponifiable materials which are used according to the invention.

Thus the following components are advantageously associated with:

tocopherols or tocotrienols, especially vitamin E, polyunsaturated fatty acids of the n-3 and n-6 series, or oils or plant extracts containing them, glycolipids such as ceramides, cerebrosides and glycosylceramides of vegetable or animal origin.

These components are generally dissolved in the lipophilic phase before preparation of the cosmetic composition.

More precisely:

Tocopherols and tocotrienols are 8-methyl-chroman-6-ols substituted in the 1-position by a methyl group and a saturated (tocopherols) or triunsaturated (tocotrienols) chain of the polyisoprene type containing sixteen carbon atoms; the alpha, beta, gamma and delta varieties differ from one another in the number and location of the methyl groups in the 5- and 7-positions.

Tocopherols and tocotrienols generally represent 200 to 1200 mg per kg of unrefined vegetable oil and are also present in certain animal (fish) oils.

Tocopherols are conventionally present in numerous oils and fats, particularly sunflower.

Tocotrienols are more rarely found, but are present especially in oils and particularly in wheat-germ and palm oils.

These constituents have recognized antioxidizing properties. Alpha-tocopherol is better known by the name vitamin E.

As their name suggests, polyunsaturated fatty acids of the n-3 and n-6 family are fatty acid acids having several units of unsaturation on their carbon chain.

Moreover, for the n-3 (or n-6) family, the first double bond is located between the 3rd (or 6th) and 4th (or 7th) carbon atoms, counting from the methyl group of the carbon chain.

The most common fatty acids of the n-6 family are linoleic acid, C18:2 (n-6, 9), gamma-linolenic acid, C18:3 (n-6, 9, 12), and arachidonic acid, C20:4 (n-6, 9, 12, 15).

The most common fatty acids of the n-3 family are alpha-linolenic acid, C18:3 (n-3, 6, 9), eicosapentaenoic acid or EPA, C20:5 (n-3, 6, 9, 12, 15), and docosahexaenoic acid or DHA, C22:6 (n-3, 6, 9, 12, 15, 18).

Glycolipids represent a valuable fraction of the polar lipids extracted from certain higher plants (leaves, roots, seeds, algae, yeasts, fungus); wheat, in particular, is a recognized source and contains about 3% of glycolipids, based on the total lipids.

The following will be chosen from the numerous constituents of this family:

ceramides: a combination of an amino alcohol of the sphingosine type with a fatty acid bonded to the amine group to form an amide;

cerebrosides or glycosylceramides: ceramides in which the primary alcohol group is etherified with a sugar (monohexoside, polyhexoside ceramides).

These sphingolipids (ceramides and cerebrosides) possess a variety of recognized properties, including an anti-free radical activity, an antielastase power and a moisturizing action.

The Examples which follow are given without implying a limitation and purely by way of illustration of the invention.

EXAMPLES

The percentages indicated in the results and compositions below are expressed by weight, unless indicated otherwise.

In all the Examples, the unsaponifiable materials are assayed according to the standard AFNOR NF T 60205-1, which is the reference method involving extraction with diethyl ether after saponification in an ethanolic medium.

The oleic acidity is determined according to the standard AFNOR NF T 60-204 by the diethyl ether/ethanol mixture method.

The separations by thin layer chromatography are carried out on 0.25 mm thick silica gel plates (type 60, MERCK). The eluent is an 80:20 (v/v) hexane/ethyl acetate mixture and the spots are developed by spraying with a 50% $H_2SO_4$ solution and mineralization at 150° C.

The constituents are identified by comparison of the retention distances with those of the following reference products: oleyl alcohol, cholesterol, squalene, eicosene, β-amyrin, triglycerides and oleic acid.

The composition in respect of free fatty acids, monoglycerides, diglycerides, triglycerides and sterols is determined by gas chromatography on a short capillary column (7 m) with an SE30 apolar stationary phase, after formation of the TMS derivatives of the compounds.

The injection is of the "on-column" type, the FID is set at 350° C. and the analysis is performed with temperature programming (100° to 340° C.).

The constituents are identified by their retention times.

The results are standardized to 100 (percentage composition).

Example 1 a) Experiment 1

50 g of shea butter containing 7% of unsaponifiable material are dissolved in 500 ml of acetone. The acetone is boiled for 15 min to recover a residue (I) insoluble in the hot acetone, and an acetone solution (S), which is cooled to –20° C.

The mixture (S) is kept at –20° C. for 12 h.

After precipitation, the supernatant is filtered off.

The precipitate is rinsed with several volumes of (cold) acetone. After evaporation of the solvent under vacuum, the filtrate is dried and then weighed.

Table I gives the results of this experiment.

Analysis of the residue (I) shows that this hot-insoluble fraction represents strongly apolar unsaponifiable constituents of the gum or latex type containing the karitene inter alia. This hot-insoluble fraction is mixed with the cold-soluble fraction.

b) Experiment 2

The procedure is as in Experiment 1 except that the starting material is 100 g of shea butter dissolved in 500 ml of acetone.

The results are collated in Table I.

c) Experiment 3

The procedure is as in Experiment 1 except that the crystallization is effected at –10° C.

The results are collated in Table I.

TABLE I

| Exp. no. | Yield of acetone-soluble fraction | Content of unsaponifibale material in the acetone-soluble fraction (purity) | Weight of unsaponifiable material obtained (W1) | Theoretical total weight of unsaponifiable material (W2) | Yield of unsaponifiable material (W1/W2 × 100)% |
|---|---|---|---|---|---|
| 1 | 18.2% | 22.95% | 2.1 g | 3.5 g | 60.0% |
| 2 | 14.7% | 23.60% | 3.5 g | 7 g | 49.6% |
| 3 | 24.5% | 16.30% | 2.0 g | 3.5 g | 57.1% |

Example 2

The procedure is as in Example 1 and the 3 Experiments below, no. 4, 5 and 6, are carried out to show the effect of dilution of the shea butter in acetone. In these Experiments, the stage of cold fractionation of the hot-soluble fraction is carried out at $-20°$ C.

The results are collated in Table II below, in which the percentages are given by weight.

TABLE II

Choice of dilution (acetone, temperature: $-20°$ C.)

| Experiment no. | Dilution (%) | Yield of soluble fraction (%) | Content of unsaponifiable material in the soluble fraction (%) | Yield of unsaponifiable material (%) |
|---|---|---|---|---|
| 4 | 5 | 16.0 | 20.6 | 47.1 |
| 5 | 10 | 18.2 | 23.0 | 59.8 |
| 6 | 20 | 14.7 | 23.6 | 49.6 |

(*): (weight obtained/theoretical weight × 100)%

Example 3

The procedure is as in the previous Examples and the Experiments below (7, 8, 9) are carried out in order to show the influence of the cold fractionation temperature on the yield of cold-soluble unsaponifiable fraction (F), the content of unsaponifiable material in this soluble fraction and the yield of unsaponifiable material in this step.

TABLE III

| Experiment no. | Temperature (°C.) | Yield of soluble fraction (%) | Content of unsaponifiable material in the soluble fraction (%) | Yield of unsaponifiable material (%) |
|---|---|---|---|---|
| 7 | $-10°$ C. | 24.5 | 16.3 | 57.1 |
| 8 | $-20°$ C. | 13.1 | 22.5 | 42.1 |
| 9 | $-30°$ C. | 7.7 | 37.2 | 40.9 |

(*): (weight obtained/theoretical weight × 100)%

The crystallization temperature is a very influential factor in the fractionation efficacy.

Lowering the temperature to $-30°$ C. makes it possible to obtain a fraction with a purity of more than 35% in respect of unsaponifiable materials, representing a 5-fold enrichment relative to the starting crude butter.

Example 4

In the following Experiments 10, 11 and 12, three different qualities of shea butter, whose characteristics are given in Table IV below, are treated by the process of the invention:

TABLE IV

| | Oleic acidity (%) | Content of unsaponifiable material (%) |
|---|---|---|
| Crude butter | 5.3 | 7.0 |
| Neutralized butter | 0.37 | 6.1 |
| Refined butter | 0.13 | 6.6 |

The results obtained are given in Table V.

TABLE V

Acetone crystallization experiments on different working materials

| Exp. no. | Working material (oleic acidity) | Yield of soluble fraction (%) | Oleic acidity of the soluble fraction (%) | Content of unsaponifiable material in the soluble fraction (%) |
|---|---|---|---|---|
| 10 | crude butter (*) | 13.1 | 20.3 | 22.5 |
| 11 | neutralized butter (0.37) (**) | 13.5 | ≈2.0 | 23.3 |
| 12 | refined butter (0.13) (*) | 11.5 | 0.9 | 25.9 |

(*): dilution: 10%, temperature: $-20°$ C.
(**): dilution: 20%, temperature: $-15°$ C.

These experiments show that the purity of the acetone-soluble fraction in respect of unsaponifiable material depends little on the nature of the starting material (crude, semirefined or refined).

Example 5

Two crude shea butters (A and B) and one neutralized and decolorized butter (C) were chosen. Their physicochemical characteristics are given in Table VI. The unsaponifiable material was analyzed by thin layer chromatography in order to show the greater or lesser proportion of apolar constituents, namely "gums" or karitenes. The semiquantitative results are given in Table VI, in which "+" denotes "presence" and "+++" denotes "very strong presence".

TABLE VI

| Nature of the sample | Oleic acidity (%) | Content of unsaponifiable material (%) | TLC analysis of the unsaponifiable material | |
|---|---|---|---|---|
| | | | Sterols, alcohols | "gums, karitenes" |
| A | 5.3 | 6.4 | + | +++ |
| B | 6.5 | 8.4 | + | +++ |
| C | 0.42 | 6.4 | + | ++ |

Crystallization was effected at $-30°$ C. on a 50 g sample with a 10% dilution in acetone.

The fraction insoluble in hot acetone (gums) was separately recovered by solubilization in hot chloroform and was then added to the cold-soluble fraction.

The results obtained are given in Table VII, which corresponds to Experiments 13, 14 and 15 performed with the above butters A, B and C respectively.

TABLE VII

Acetone crystallization experiments at −30° C.
(dilution: 10%)

| Exp. no. | Working material | Nature of the fraction | Content based on the butter (%) | | Oleic acidity (%) | Content of unsaponifiable material (%) |
|---|---|---|---|---|---|---|
| 13 | A | Hot-insoluble (gums) | 5.8 | 17.2 | 18.7 | ≈35 |
|  |  | Cold-soluble (unsaponifiable material) | 11.4 |  |  |  |
|  |  | Cold-insoluble (oil) | 82.8 |  | 2.8 | 1.4 |
| 14 | B | Hot-insoluble (gums) | 7.4 | 20.6 | 17.1 | ≈46 |
|  |  | Cold-soluble (unsaponifiable material) | 13.2 |  |  |  |
|  |  | Cold-insoluble (oil) | 79.4 |  | 3.6 | 1.7 |
| 15 | C | Hot-insoluble (gums) | 5.5 | 13.4 | 2.4 | ≈34 |
|  |  | Cold-soluble (unsaponifiable material) | 7.9 |  |  |  |
|  |  | Cold-insoluble (oil) | 86.6 |  | 0.2 | 1.9 |

The results obtained are entirely consistent.

The contents of unsaponifiable materials attained are greater than 30% and the fractions enriched with unsaponifiable materials correspond to + than 10% of starting shea butter.

It is noted that the free acidity of the fraction obtained from the decolorized neutralized butter is about 2%.

The purities in respect of unsaponifiable material show that a yield of >70% is attained for all the experiments, showing the effectiveness of recycling the hot-insoluble fraction (gums).

The determinations of the exact content of unsaponifiable material according to the standard are difficult precisely because of the presence of these gums insoluble in the solvent phase (unsaponifiable material) and in the aqueous-alcoholic phase (fatty acid soaps).

For this reason the values found may be under-evaluations, even on shea butter as such.

Analysis by thin layer chromatography shows that
the cold-insoluble fractions almost exclusively consist of triglycerides; traces of unsaponifiable material (fatty alcohols and sterols) are apparent;
the fractions resulting from the mixing of the hot-insoluble materials and cold-soluble materials consist of the following, in order of decreasing polarity: sterols, free fatty acids, aliphatic and triterpene fatty alcohols, triglycerides and very apolar constituents. The latter correspond to the hot-insoluble fraction, i.e. the karitenes or gums.

The same TLC analysis performed on the unsaponifiable materials shows that the latter, which remain in the cold-insoluble fraction in a proportion of about 1.5–2%, consist of alcohols and sterols. No gums remain, while the unsaponifiable part concentrated in the cold-soluble fraction contains the fatty alcohols, the sterols and the gums.

Analysis by gas chromatography makes it possible to obtain the percentage composition of the different constituents of the fractions in the absence of the gums, whose very high molecular weight is not compatible with gas chromatography.

The constituents separable by chromatography are:
the triglycerides,
the free fatty acids,
the partial glycerides,
the unsaponifiable material: sterols and fatty alcohols.

This analysis confirms
the virtual absence of unsaponifiable materials in the cold-insoluble fractions.
the concentration, in the fractions enriched with unsaponifiable materials, of the free fatty acids and the partial glycerides in the presence of triglycerides.

The percentage compositions obtained are given in Table VIII.

TABLE VIII

Percentage compositions (%) of the different fractions obtained by GC on SE$_{30}$ apolar stationary phase (gums or karitenes not chromatographed)

| Sample ref. | Fraction ref. | Free fatty acids | Monoglycerides | Diglycerides | Triglycerides | Unsaponifiable material "sterols + alcohols" |
|---|---|---|---|---|---|---|
| A | Hot-insoluble + cold-soluble | 24.5 | 0.2 | 22.1 | 41.0 | 9.8 |
|  | Cold-insoluble | 7.4 | 0.2 | 8.3 | 82.0 | 2.1 |
| B | Hot-insoluble + cold-soluble | 23.2 | 0.7 | 23.5 | 42.5 | 10.2 |
|  | Cold-insoluble | 4.0 | <0.1 | 2.2 | 93.6 | 0.2 |
| C | Hot-insoluble + cold-soluble | 2.0 | 0.1 | 28.4 | 57.2 | 12.3 |
|  | Cold-insoluble | 0.3 | <0.1 | 1.7 | 97.7 | 0.3 |
| Control:* |  | 3.1 | <0.1 | 1.6 | 95.2 | 0.1 |

*This product is crude shea butter as such, unfractionated, as described in Table IV.

Analyses by HPLC further confirm that
1) the hot-insoluble fraction corresponds to the karitenes (gums).
2) the fractions enriched with unsaponifiable material contain all the native constituents of the unsaponifiable material of shea:
   * karitenes (gums),
   * triterpene alcohols,
   * sterols.

Example 6

A crystallization experiment was performed on 3 kg of neutralized and decolorized shea butter corresponding to the specifications of the product C of Example 5.

The following operating conditions were observed:
sample: 3×1 kg,
execution in 3 batches of 5×200 g,
volume of acetone: 1l per 200 g, i.e. a dilution of 20%,
hot solubilization of the shea butter (at the boil), with stirring,
decantation: 15 min,
recovery of the insoluble fraction (gums) with chloroform,
crystallization: −30° C., 12 h,
filtration (without rinsing of the precipitate),
evaporation of the acetone,
mixing of the (hot-insoluble)+(cold-soluble) fractions in chloroform,
evaporation+drying.

The following results are obtained:
weight of fraction enriched with unsaponifiable materials: about 150 g, yield of fraction enriched with unsaponifiable materials: 5%,
appearance of the fraction enriched with unsaponifiable materials: thick yellow oil,
purity of the fraction enriched with unsaponifiable materials in respect of the latter: greater than 48%.

Example 7

Anhydrous composition (in the form of a balm)

Compositions in the form of a balm, whose composition by weight is given below, are prepared by simply mixing the constituents indicated below at a temperature of between 40° and 50° C.:
shea butter fraction enriched with unsaponifiable material: 1–60%, preferably 5%
petrolatum: 30–60%
paraffin wax: 0–30%
perfume: 1–3%
vitamin E: 0–1%
glycolipids or sphingolipids: 0–2%
fish oil: 0–1%
In these compositions, the shea butter fraction enriched with unsaponifiable material consists of the mixture of hot-insoluble fractions (I) and cold-soluble fractions (I') obtained in each of Examples 1 to 6.

Example 8

Face and body oil

The following compositions are prepared from the same fractions enriched with unsaponifiable material as in Example 7:
enriched shea butter fraction: 2–10, preferably 5%
liquid petrolatum: 90–95
fish oil: 1%
vitamin E: 1%
glycolipids or sphingolipids: 0–2%.

Example 9

Care creme: water-in-oil emulsion

The following compositions are prepared from the same fractions enriched with unsaponifiable material as in Example 7:
enriched shea butter fraction: 10–25, preferably 15%
liquid petrolatum: 10–15%
cetyl alcohol: 4%
sorbitan stearate: 3%
vitamin E: 0–1%
fish oil: 0–1%
glycolipids or sphingolipids: 0–2% water, perfume, preservatives qsp 100

Example 10

Care creme: oil-in-water emulsion

The following compositions are prepared from the same fractions enriched with unsaponifiable material as in Example 7:
shea butter fraction: 10–20%, preferably 15%
cetyl alcohol: 3%
triethanolamine: 1%
glycerol stearate: 3%
colorant: 3%
vitamin E: 0–1%
glycolipids or sphingolipids: 0–2%
fish oil: 0–1%
water, perfume, preservatives qsp 100

What is claimed is:

1. A process for the preparation of a fat fraction of vegetable origin enriched with unsaponifiable materials, comprising the steps of:
treating a fat of vegetable origin with a hot polar solvent of the ketone type to obtain a first fraction insoluble in said hot ketone solvent which is rich in unsaponifiable materials, and a second fraction comprising a solution of hot soluble materials;
separating said first fraction from the second fraction of hot soluble materials;
subjecting said second fraction to crystallization in a crystallization solvent at a temperature below 0° C., followed by filtering to obtain a filtrate; and
evaporating the crystallization solvent from the filtrate to obtain a further fraction rich in unsaponifiable materials.

2. A process according to claim 1, wherein the treating with the hot polar solvent is carried out at the boiling point of said hot polar solvent.

3. A process according to one of claim 1, wherein the hot ketone solvent is a ketone containing at most ten carbon atoms.

4. A process according to claim 1, wherein the ketone solvent is acetone.

5. A process according to claim 1, wherein the crystallization is carried out at a temperature below −15° C.

6. A process according to claim 5, wherein the crystallization is carried out at a temperature of between −15° and −30° C.

7. A process according to claim 1, wherein the fat is a fat originating from seeds or fruits of oleaginous plants, obtained by a pressure or pressure/extraction technique, said fat being either crude or refined beforehand.

8. A process according to claim 1, wherein the fat is shea butter.

9. A process according to claim 8 wherein the shea butter is crude.

10. A process according to claim 8, additionally comprising refining said shea butter before said treating, in order to retain a maximum amount of unsaponifiable material therein and preserve constituents of the shea butter.

11. A process according to claim 1, further comprising mixing at least part of said first fraction and said further fraction which are rich in unsaponifiable materials.

12. A process according to claim 11, wherein the fat is shea butter.

13. A cosmetic composition comprising as an active ingredient a cosmetically effective amount of a mixture of fractions rich in unsaponifiable materials, obtained according to the process of claim 12.

14. A pharmaceutical composition comprising as an active ingredient a pharmaceutically effective amount of a mixture of fractions rich in unsaponifiable materials, obtained according to the process of claim 12.

15. A composition according to claim 13 or 14, wherein the mixture of fractions contains 18 to 50% by weight of unsaponifiable materials.

16. A composition according to claim 15, wherein the mixture of fractions contains 20 to 50% by weight of unsaponifiable materials.

17. A composition according to claim 13 or 14, wherein the mixture of fractions contains about 30% by weight of unsaponifiable materials.

18. A composition according to claim 13 or 14, containing about 0.5 to 99% by weight of said mixture in an acceptable excipient, vehicle or solvent.

19. A composition according to claim 13 or 14, containing about 2 to 60% by weight of said mixture.

20. A composition according to claim 13 or 14, additionally comprising at least one component selected from the group consisting of tocopherols, tocotrienols, polyunsaturated fatty acids of the n-3 or n-6 series, oils or plant extracts containing polyunsaturated fatty acids of the n-3 or n-6 series, glycolipids and sphingolipids.

21. The composition according to claim 20, wherein the tocopherol is vitamin E.

22. A method of cosmetic treatment comprising applying to living skin a composition containing a cosmetically effective amount of a mixture of fractions rich in unsaponifiable materials obtained according to the process of claim 12.

23. A method of therapeutic treatment comprising applying to living skin a composition containing a dermatologically effective amount of a mixture of fractions rich in unsaponifiable materials obtained according to the process of claim 12.

24. A process according to claim 1, wherein the crystallizing is carried out in a crystallization solvent which is any solvent for the hot soluble materials.

25. A process according to claim 24, wherein the crystallization is carried out directly on the solution of hot soluble materials in the ketone solvent separated from said first fraction.

26. A process according to claim 25, wherein the ketone solvent is acetone.

* * * * *